United States Patent
Cunliffe et al.

(10) Patent No.: US 10,085,780 B2
(45) Date of Patent: Oct. 2, 2018

(54) BONE FIXATION DEVICE

(71) Applicants: Mark Richard Cunliffe, Huddersfield (GB); Malcolm Graham Ness, Morpeth (GB)

(72) Inventors: Mark Richard Cunliffe, Huddersfield (GB); Malcolm Graham Ness, Morpeth (GB)

(*) Notice: Subject to any disclaimer, the term of this patent is extended or adjusted under 35 U.S.C. 154(b) by 140 days.

(21) Appl. No.: 14/926,144

(22) Filed: Oct. 29, 2015

(65) Prior Publication Data

US 2016/0045235 A1    Feb. 18, 2016

Related U.S. Application Data

(63) Continuation-in-part of application No. 13/098,087, filed on Apr. 29, 2011, now abandoned, which is a (Continued)

(30) Foreign Application Priority Data

May 26, 2006 (GB) .................................. 0610630.6

(51) Int. Cl.
*A61B 17/80* (2006.01)
*A61B 17/84* (2006.01)

(52) U.S. Cl.
CPC .......... *A61B 17/8085* (2013.01); *A61B 17/80* (2013.01); *A61B 17/8057* (2013.01)

(58) Field of Classification Search
CPC . A61B 17/8085; A61B 17/80; A61B 17/8014; A61B 17/8052; A61B 17/8057
See application file for complete search history.

(56) References Cited

U.S. PATENT DOCUMENTS 3,322,449 A    5/1967  Becker
3,603,626 A    9/1971  Whiteside
(Continued)

FOREIGN PATENT DOCUMENTS

DE    9 004 960 U1    8/1991
EP    0 491 983 A1    7/1992
(Continued)

OTHER PUBLICATIONS

United Kingdom Search Report for Application No. GB0610630.6 dated Nov. 27, 2006, 1 page.
(Continued)

*Primary Examiner* — Jacqueline Johanas
(74) *Attorney, Agent, or Firm* — Howard & Howard Attorneys PLLC

(57) ABSTRACT

A bone fixation device includes a plastically deformable bone fixation body having a screw receiving aperture extending therethrough. The shape of the aperture is defined by a side wall having a first threaded portion, a second smooth walled portion extending from the first threaded portion, and a third smooth walled portion extending from the second portion. The aperture has a step change in cross section between the second and third portions defining a lip. The second and third portions are connected by a lip face extending substantially normal to the aperture length with the edge of the lip face defining the lip. The device further includes at least one bone fixation screw having a shaft and a head. The shaft engages with the first threaded portion of the aperture and the head abuts the lip with an abutment force being directed substantially radially outwards so producing a tight fit.

6 Claims, 11 Drawing Sheets

Related U.S. Application Data continuation-in-part of application No. 12/302,586, filed as application No. PCT/GB2007/001912 on May 21, 2007, now abandoned.

(56) References Cited

U.S. PATENT DOCUMENTS

| | | | |
|---|---|---|---|
| 3,921,364 A | 11/1975 | Briles |
| 4,219,015 A | 8/1980 | Steinemann |
| 4,484,570 A | 11/1984 | Sutter et al. |
| 4,702,658 A | 10/1987 | Salter |
| 4,750,851 A | 6/1988 | Thomey |
| 4,905,679 A | 3/1990 | Morgan |
| 5,053,036 A | 10/1991 | Perren et al. |
| 5,269,784 A | 12/1993 | Mast |
| 5,336,224 A | 8/1994 | Selman |
| 5,389,099 A | 2/1995 | Hartmeister et al. |
| 5,569,251 A | 10/1996 | Baker et al. |
| 5,616,144 A | 4/1997 | Yapp et al. |
| 5,904,684 A | 5/1999 | Rooks |
| 6,004,353 A | 12/1999 | Masini |
| 6,022,350 A | 2/2000 | Ganem |
| 6,039,740 A | 3/2000 | Olerud |
| 6,065,614 A | 5/2000 | Gunther et al. |
| 6,228,085 B1 | 5/2001 | Theken et al. |
| 6,293,949 B1 | 9/2001 | Justis et al. |
| 6,322,562 B1 | 11/2001 | Wolter |
| 6,423,068 B1 | 7/2002 | Reisberg et al. |
| 6,613,053 B1 | 9/2003 | Collins et al. |
| 6,656,181 B2 | 12/2003 | Dixon et al. |
| 6,730,091 B1 | 5/2004 | Pfefferle et al. |
| 6,761,719 B2 | 7/2004 | Justis et al. |
| 6,821,279 B2 | 11/2004 | Di Emidio |
| 6,908,272 B2 | 6/2005 | Nilsen et al. |
| 7,052,499 B2 | 5/2006 | Steger et al. |
| 7,104,991 B2 | 9/2006 | Dixon et al. |
| 7,229,446 B2 | 6/2007 | Capanni |
| 7,716,805 B2 | 5/2010 | Hommel |
| 7,740,634 B2 | 6/2010 | Orbay et al. |
| 7,766,947 B2 | 8/2010 | Hawkes et al. |
| 7,905,883 B2 | 3/2011 | Bruecker et al. |
| 7,909,859 B2 | 3/2011 | Mosca et al. |
| 7,951,178 B2 | 5/2011 | Jensen |
| 8,172,885 B2 | 5/2012 | Songer et al. |
| 8,177,820 B2 | 5/2012 | Anapliotis et al. |
| 8,337,506 B2 | 12/2012 | Cunliffe et al. |
| 8,460,345 B2 | 6/2013 | Steger et al. |
| 8,574,272 B2 | 11/2013 | Wallenstein et al. |
| 2002/0131842 A1 | 9/2002 | Eriksson |
| 2002/0193769 A1 | 12/2002 | Emidio |
| 2003/0074004 A1 | 4/2003 | Reed |
| 2003/0078583 A1 | 4/2003 | Biedermann et al. |
| 2003/0153912 A1 | 8/2003 | Graf |
| 2004/0034353 A1 | 2/2004 | Michelson |
| 2004/0111089 A1 | 6/2004 | Stevens et al. |
| 2004/0181226 A1 | 9/2004 | Michelson |
| 2004/0215192 A1 | 10/2004 | Justis et al. |
| 2004/0236327 A1 | 11/2004 | Paul et al. |
| 2005/0015090 A1 | 1/2005 | Silverman |
| 2005/0059970 A1 | 3/2005 | Kolb |
| 2005/0065515 A1 | 3/2005 | Jahng |
| 2005/0187551 A1 | 8/2005 | Orbay et al. |
| 2005/0187552 A1 | 8/2005 | Michelson |
| 2005/0192578 A1 | 9/2005 | Horst |
| 2005/0245931 A1 | 11/2005 | Orbay |
| 2005/0261780 A1 | 11/2005 | Heino et al. |
| 2005/0273104 A1 | 12/2005 | Oepen et al. |
| 2006/0004361 A1 | 1/2006 | Hayeck et al. |
| 2006/0009771 A1 | 1/2006 | Orbay et al. |
| 2006/0089648 A1 | 4/2006 | Masini |
| 2006/0129151 A1 | 6/2006 | Allen et al. |
| 2006/0149228 A1 | 7/2006 | Schlapfer et al. |
| 2006/0229619 A1 | 10/2006 | Orbay et al. |
| 2006/0259039 A1 | 11/2006 | Pitkanen et al. |
| 2006/0264948 A1 | 11/2006 | Williams |
| 2007/0162020 A1 | 7/2007 | Gerlach et al. |
| 2007/0276386 A1 | 11/2007 | Gerlach et al. |
| 2008/0051786 A1 | 2/2008 | Jensen |
| 2008/0234751 A1 | 9/2008 | McClintock |
| 2008/0294165 A1 | 11/2008 | Cunliffe et al. |
| 2009/0240287 A1 | 9/2009 | Cunliffe et al. |
| 2009/0306723 A1 | 12/2009 | Anapliotis et al. |
| 2010/0211111 A1 | 8/2010 | Sonntag et al. |
| 2012/0029576 A1 | 2/2012 | Cunliffe et al. |
| 2014/0128871 A1 | 5/2014 | Orbay |

FOREIGN PATENT DOCUMENTS

| | | |
|---|---|---|
| GB | 2 125 295 A | 3/1984 |
| GB | 2 405 342 A | 3/2005 |
| JP | H 10-043202 A | 2/1998 |
| WO | WO 99/05982 A1 | 2/1999 |
| WO | WO 00/40167 A1 | 7/2000 |
| WO | WO 2005/030029 A2 | 4/2005 |
| WO | WO 2005/122965 A2 | 12/2005 |
| WO | WO 2005/122965 A3 | 12/2005 |
| WO | WO 2007/138270 A2 | 12/2007 |
| WO | WO 2007/138270 A3 | 12/2007 |

OTHER PUBLICATIONS

United Kingdom Search Report for Application No. GB0709693.6 dated Aug. 24, 2007, 2 pages.

International Search Report for Application No. PCT/GB2007/001912 dated Feb. 19, 2008, 7 pages.

Machine-assisted English translation for DE 9 004 960 extracted from espacenet.com database on Feb. 4, 2016, 5 pages.

English language abstract and machine-assisted English translation for JPH 10-043202 extracted from PAJ database on Feb. 4, 2016, 28 pages.

BONE FIXATION DEVICE

The subject patent application is a continuation-in-part of co-pending U.S. patent application Ser. No. 13/098,087, filed on Apr. 29, 2011, which is a continuation-in-part of U.S. patent application Ser. No. 12/302,586, filed on May 26, 2009, now abandoned, which is the National Stage and claims priority to and all the advantages of International Patent Application No. PCT/GB07/01912, filed on May 21, 2007, which claims priority to U.K. Application No. 0610630.6, filed on May 26, 2006, the disclosures of which are hereby incorporated by reference.

The present invention relates to a bone fixation device. More particularly, but not exclusively, the present invention relates to a bone fixation device having at least one aperture extending therethrough, and a bone fixation screw. The screw and the aperture each comprise a threaded portion and a smooth portion, the smooth portion of the screw being adapted to radially abut the smooth portion of the aperture as the respective threaded portions are threaded into interengagement.

Bone fixation devices having apertures extending therethrough for receiving bone fixation screws are known. U.S. Pat. No. 5,336,224 discloses a bone fixation device comprising a plurality of screw receiving members connected together in a line by connecting arms. Extending through each screw receiving member is a screw receiving aperture. Each aperture comprises a threaded portion and a bowl shaped smooth portion. In use a screw is threaded into engagement with the screw receiving aperture. As the screw head is received in the bowl, the head urges the bowl forwards in the direction of the axis of the screw until the bone fixation device abuts the bone. The head is then tightened in the bowl.

Such a bone fixation device must be perfectly matched to the profile of the bone. If the two are not perfectly matched then as one screw is tightened urging the bone fixation device into contact with the bone then displacement of the bone fixation device may pull a previously tightened screw out of engagement with the bone. This can be a particular problem for elderly patients or patients with low bone density.

The bone fixation device according to the invention seeks to overcome the problems of the prior art.

Accordingly, in a first aspect, the present invention provides a bone fixation device comprising
a plastically deformable bone fixation body having at least one screw receiving aperture extending therethrough;
the shape of the aperture being defined by a side wall, the side wall comprising a first threaded portion, a second smooth walled portion extending from the first threaded portion and a third smooth walled portion extending from the second smooth walled portion;
the aperture having a step change in cross section between the second and third smooth walled portions defining a lip for abutment with the head of the screw, the step change being a discontinuity in the size of the aperture at the lip with the third portion being larger than the second portion, the second and third portions being connected by a lip face which extends substantially normal to the length of the aperture, the edge of the lip face defining the lip; and,
at least one bone fixation screw, the screw comprising a threaded shaft and a head, the shaft being adapted to engage with the first threaded portion of the aperture and the head being adapted to abut the lip with an abutment force, the abutment force being directed substantially radially outwards so producing a tight fit.

As a bone fixation screw is threaded into engagement with the screw receiving aperture of the bone fixation device according to the invention the head of the screw abuts the lip. The combination of threaded engagement of screw receiving aperture and screw and abutment of screw receiving aperture and screw head firmly locks the two together. The bone fixation device may therefore be arranged remote from the bone and locked in place by bone fixation screws. The bone fixation device therefore does not need to be exactly the same profile as the bone, considerably simplifying the surgical procedure.

Each of the portions of the aperture can be cylindrical.

The diameter of the first threaded portion can be less than the diameter of the second smooth portion.

There can be a step change between the first threaded portion and second smooth portion.

The second smooth portion can comprise a conical portion extending from the first threaded portion to a region of constant diameter of the second smooth portion.

The bone fixation body can comprise at least two screw receiving members each having a screw receiving aperture extending therethrough, the screw receiving members being connected together by a deformable connecting arm.

The bone fixation body can comprise a plurality of screw receiving members connected together in a line by a plurality of deformable connecting arms.

The screw receiving members can be substantially spherical.

A portion of the substantially spherical member can be flattened, the flattened portion being centered about a mouth of the aperture and being in a plane normal to the axis of the aperture.

The bone fixation body can be a plate.

The bone fixation body can comprise first and second laminar portions connected together by a step.

The side walls of the aperture can extend from the body.

In a further aspect of the invention there is provided a bone fixation device comprising
a plastically deformable bone fixation body having at least one screw receiving aperture extending therethrough, wherein the aperture is cylindrical and of constant area along its length;
the shape of the aperture being defined by a side wall, the side wall comprising a first threaded portion and a second smooth walled portion extending from the first threaded portion; and,
a bone fixation screw having a threaded shaft and a head, the shaft being adapted to engage with the first threaded portion to draw the head into the aperture, wherein the screw head is tapered with the diameter of the head increasing in a direction away from the threaded shaft;
the taper of the head of the screw being adapted such that as the screw head is drawn into the aperture the head abuts the second smooth walled portion with an abutment force which is directed substantially radially outwards, so locking the screw and aperture together.

Again, as the bone fixation screw is threaded into the screw receiving aperture the screw head abuts the side wall of the aperture locking the bone screw and bone fixation device together.

The plastically deformable bone fixation body can comprise a plurality of screw receiving members connected together in a line by connecting arms.

The screw receiving members can be substantially spherical.

A portion of the substantially spherical member can be flattened, the flattened portion being centered about a mouth of the aperture and being in a plane normal to the axis of the aperture.

The bone fixation body can be a plate.

The bone fixation body can comprise first and second laminar portions connected together by a step.

The present invention will now be described by way of example only and not in any limitative sense with reference to the accompanying drawings in which FIG. 1 shows a known fixation plate before and after deformation;

Figure 1:
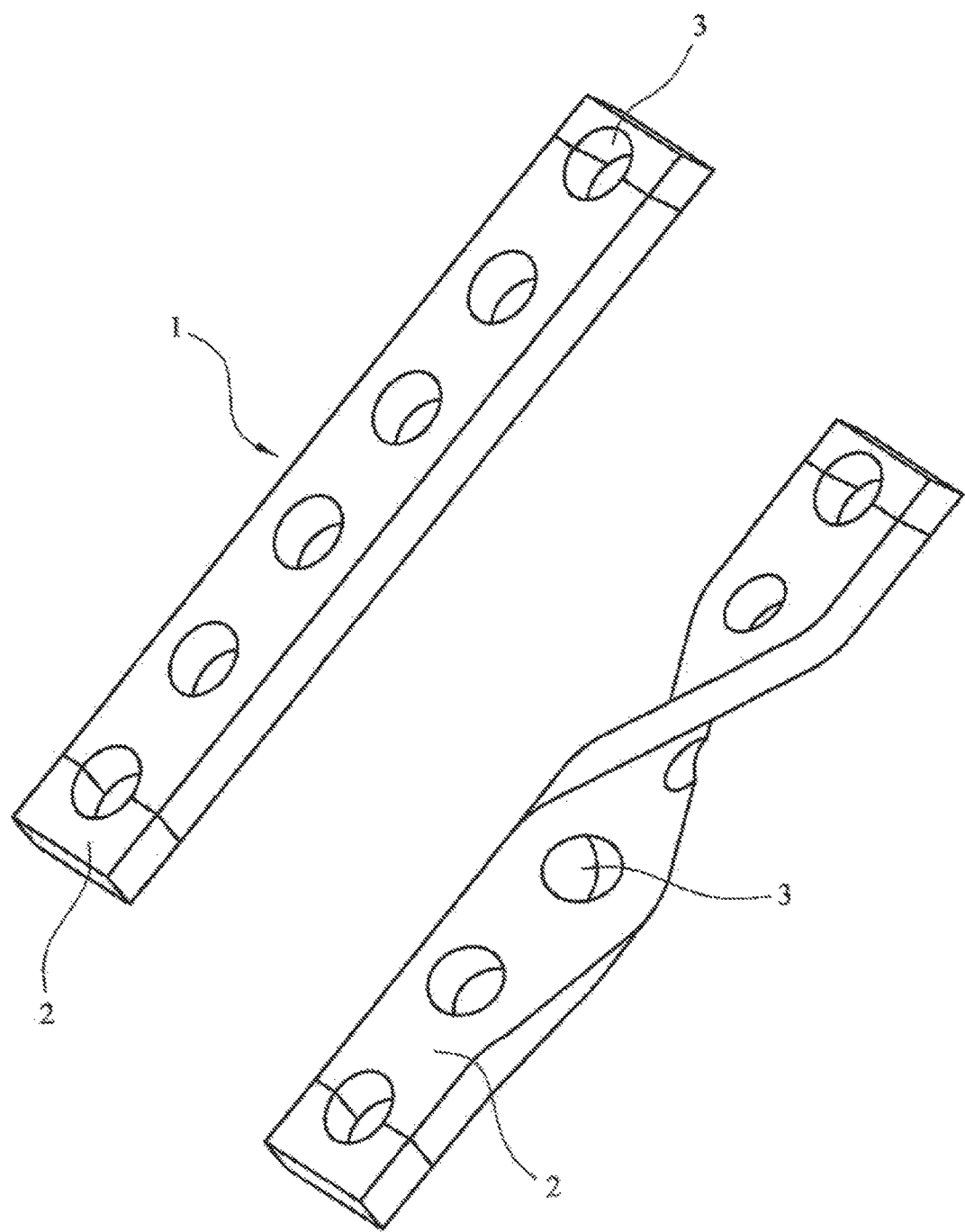

Shown in FIG. 1 is a known bone plate 1. The bone plate 1 comprises a metal plate 2 having a plurality of apertures 3. In use the bone plate 1 is placed against a bone (not shown). Bone fixation screws (not shown) are passed through the apertures 3 and then screwed into the bone. The screw heads typically engage with the plate 1 firmly fixing the plate 1 in position and preventing it from being displaced with respect to the bone.

A problem can arise however if the bone plate 1 needs to be deformed before it can be fixed to the bone. Deformation of the plate 1 deforms the apertures 3 in the plate 1 as shown. This prevents the screw heads from accurately engaging with the apertures 3 which may result in the plate 1 being free to wobble slightly with respect to the bone. This can reduce the effectiveness of the bone plate 1 as a support for the bone.

In addition, it can be difficult to remove such a known bone plate 1 from the bone when it is no longer required. The screw heads tend to cold weld to the bone plate 1 over time making the screws difficult to remove. It is often necessary to cut the bone plate 1 free which can result in damage to the bone.

Such a known bone plate 1 is also limited as to how it can be deformed. Whilst the plate 1 can be bent as shown in FIG. 1 it is not a simple matter to twist it such that the apertures 3 lie in different planes.

In addition, such a known bone fixation plate 1 comprises relatively simple threaded apertures. The fixation plate is screwed in place by threading screws into engagement with the apertures. The heads of the screws urge the bone fixation plate into abutment with the bone.

In use a surgeon must deform the plate to exactly the same profile as the bone so that all of the screws can be fully tightened. This can be time consuming and difficult for the surgeon. If the curvature of the bone fixation plate does not match the bone exactly then as one screw is tightened the plate may move causing a screw further along the plate to be pulled out of engagement with the bone.

Figure 2:
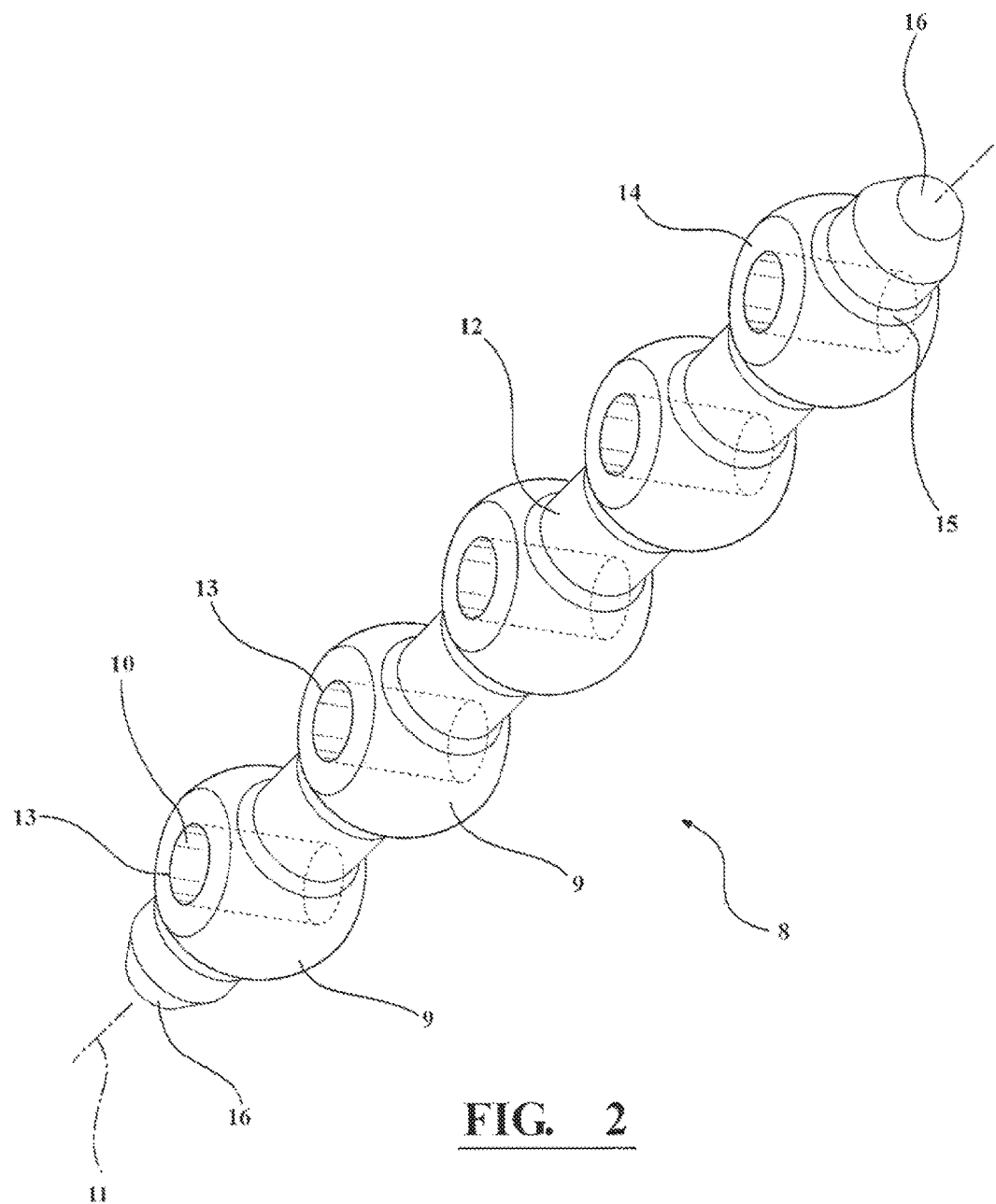
FIG. 2 shows a bone fixation device according to the invention in perspective view.

Shown in FIG. 2 is a bone fixation device 8 according to the invention. The device comprises a plastically deformable bone fixation body which comprises a plurality of screw receiving members 9. Apertures 10 extend through each of the screw receiving members 9 for receiving screws. A long axis 11 extends between each of the screw receiving members 9. Plastically deformable connecting arms 12 extend along the long axis 11 between the screw receiving members 9 as shown. In this embodiment the long axis 11 passes through the apertures 10 of the screw receiving members 9.

In use the bone fixation device 8 is gripped and bent to the required shape. The arms 12 are more pliable than the screw receiving members 9 and accordingly it is the arms 12 that bend when the force is applied, rather than the screw receiving members 9. The apertures 10 therefore remain undistorted. In addition, in contrast to known bone plates 1 a torsional (twisting) force can be applied to the device 8 rotating one or more of the screw receiving members 9 about the long axis 11 of the device 8 if required. As the long axis 11 passes along the length of the connecting arm 12, the connecting arm 12 twists about its length. The device 8 can therefore be twisted without significantly altering its dimensions. The device 8 can therefore be inserted into small apertures even after twisting.

In this embodiment of the invention each of the screw receiving members 9 is substantially spherical with the apertures 10 extending through the centers of the spheres 9. Each aperture 10 intersects the sphere at mouths 13 on opposite sides of the sphere 9. The sphere 9 comprises a slightly flattened portion 14 around one of the mouths. This reduces the profile of the device 8. It also provides an extended contact area between the screw receiving members 9 and the bone.

The connecting arms 12 between the screw receiving members 9 are cylindrical. The interface 15 between the arms 12 and spherical screw receiving members 9 is chamfered so that any bending or torsional forces do not concentrate at this interface 15.

The ends 16 of the device 8 are tapered as shown so that the device 8 can be placed between bone and soft tissue without surgically exposing the entire length of bone.

Figure 2A:
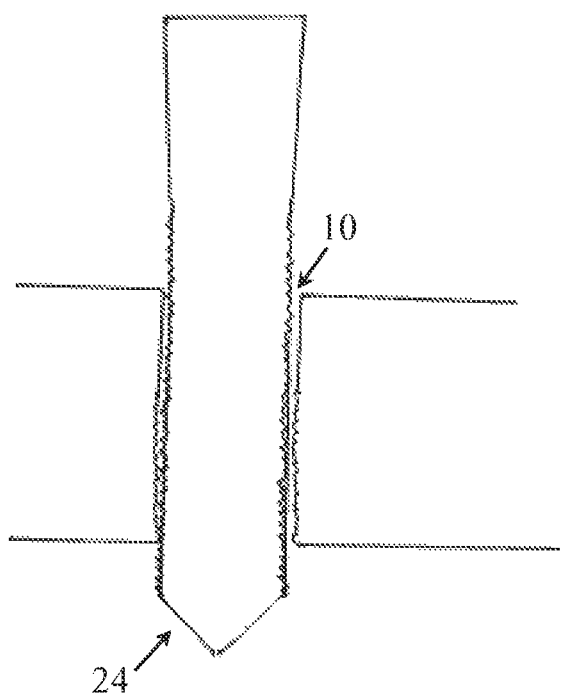
FIGS. 2A and 2B show the bone fixation device of FIG. 2 in combination with a screw.
Figure 2B:
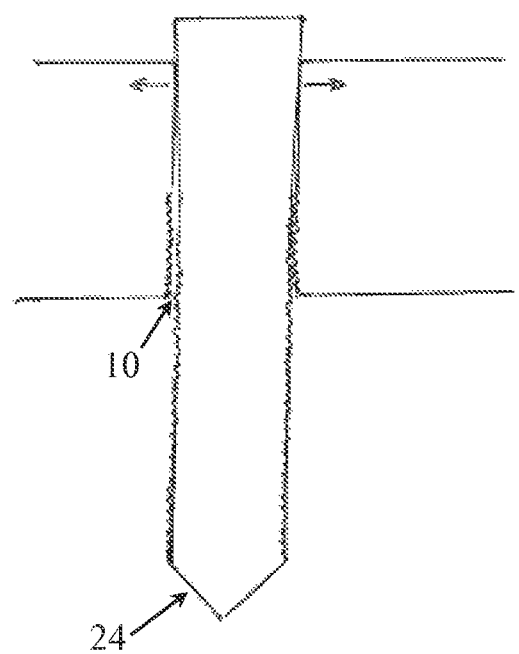

As shown in FIGS. 2A and 2B, each of the apertures 10 of this embodiment is cylindrical having a constant area along its length. A portion of the aperture 10 is threaded. The remainder of the aperture is smooth walled.

After bending and/or twisting to the correct shape the device 8 is positioned against the bone. Screws are inserted into the apparatus 10 through the smooth portions and into threaded engagement with the threaded portions. On further rotation of the screws they penetrate and grip the bone, fixing the device 8 to the bone. A significant advantage of the device 8 is that is can be bent/twisted to the correct shape, positioned correctly and then the screws inserted. This considerably simplifies the attachment procedure. As the screw receiving members 9 are aligned with the connection arms 12 along the long axis 11 the device 8 can be twisted about its length without any significant change in dimensions of the device 8. This is particularly useful when inserting the device 8 into small apertures.

The device 8 is adapted to be used with a screw (not shown) having two portions—a threaded portion for gripping the threaded portion of the aperture 10 and then the bone and a smooth head portion extending from the threaded portion. The smooth head portion has an outer face which is substantially cylindrical and of the same diameter as the threaded portion. The smooth head portion is however slightly tapered with its diameter increasing in a direction away from the threaded portion. At its end the diameter of the smooth head portion is slightly larger than the diameter of the aperture 10. As the screw is turned and is drawn into the aperture 10 the smooth head portion of the screw abuts the smooth portion of the aperture 10 so producing a press fit. This press fit firmly locks the bone fixation device 8 and screw together, even when the device 8 is remote from the bone. The bone fixation device 8 therefore does not need to exactly match the profile of the bone. This considerably simplifies the surgical procedure. The taper of the smooth head portion is very slight. Accordingly, as the head portion abuts (ie is pushed into contact with) the smooth portion this produces an abutment force which extends substantially radially outwards, so locking the screw and aperture together.

Figure 3:
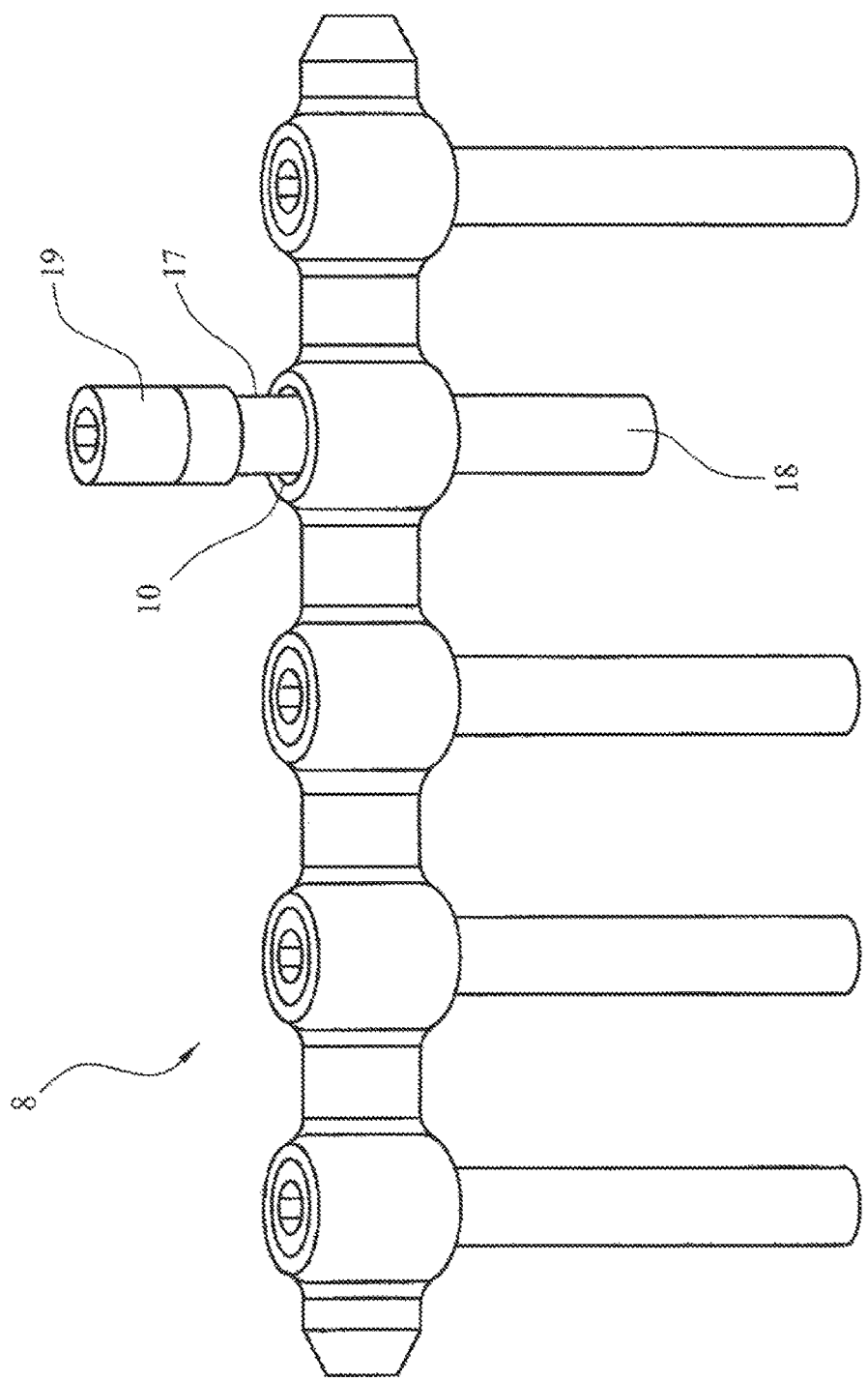
FIG. 3 shows the embodiment of FIG. 2 in combination with a screw.

An alternative embodiment of the invention is shown in FIG. 3. In this embodiment the threaded portion of the aperture 10 is narrower in diameter than the smooth portion. The screw 17 has a narrow threaded portion 18 and a wider smooth tapered head portion 19 as shown. The narrow threaded portion 18 of the screw 17 engages with the narrow portion of the aperture 10 drawing the larger smooth head portion 19 into abutment with the smooth portion of the aperture 10.

In the above embodiments the smooth portions are perfectly smooth. In alternative embodiments the smooth portions may comprise surface texture such as ripples or bevels. In a further embodiment of the invention a portion of the aperture 10 is slightly bevelled so that a standard bone screw head will press fit into engagement with the bevels as the screw is drawn into the aperture 10.

Figure 4:
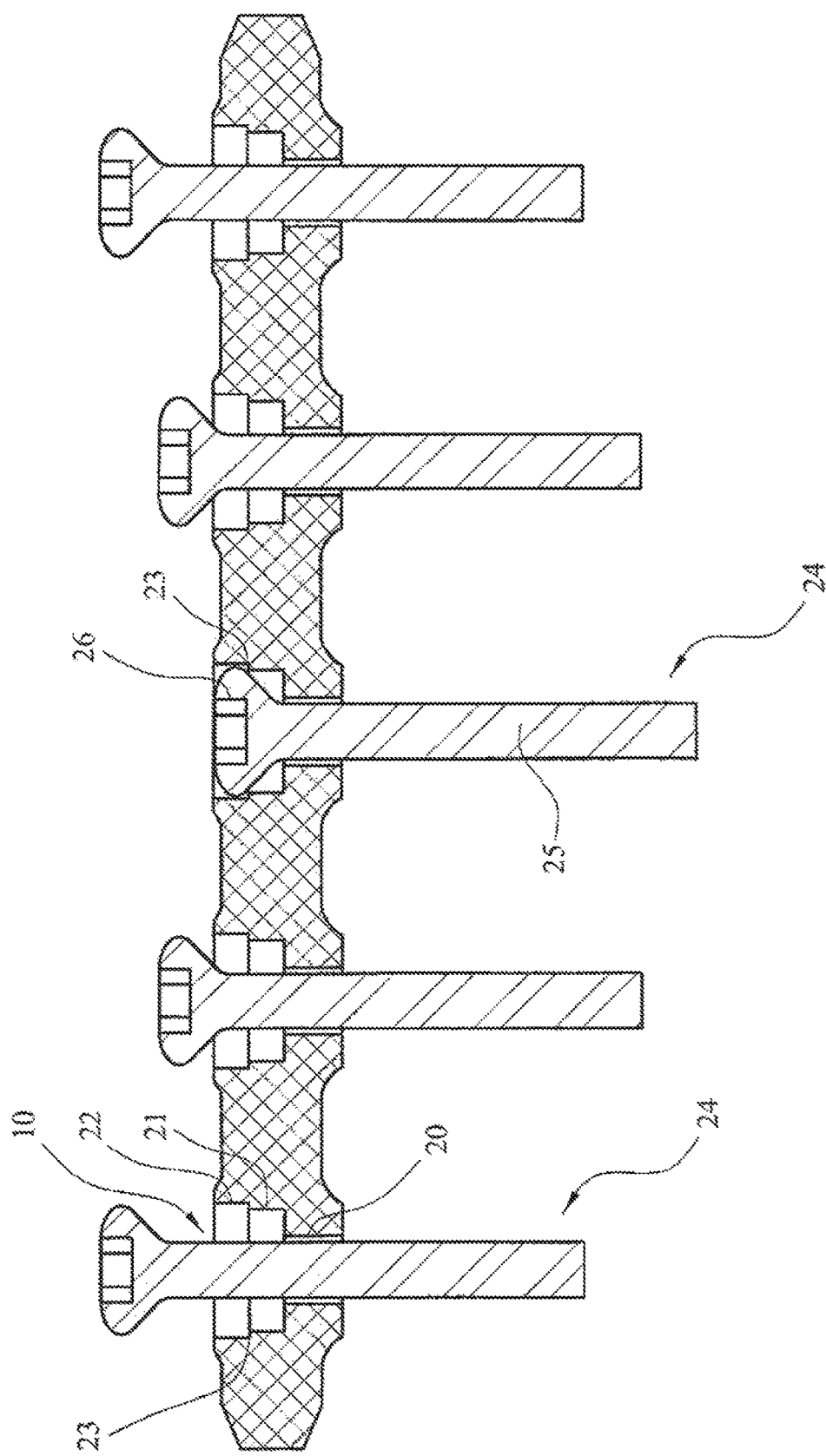
FIG. 4 shows a further embodiment of a bone fixation device according to the invention in cross sectional view.

Shown in FIG. 4 in cross sectional view is a further embodiment of a device 8 according to the invention. The aperture 10 comprises a first narrow threaded section 20. Extending from this is a second smooth walled section 21 of larger diameter. Extending from the second section 21 is a third smooth walled section 22 of slightly larger diameter than the second section 21. The step change in diameter from the second section 21 to the third section 22 defines a lip 23. In use a screw 24 is inserted into the aperture 10 with the threaded portion 25 of the screw 24 in threaded engagement with the narrower portion 20 of the aperture 10. As the screw 24 is turned and drawn in to the aperture 10 the head 26 of the screw 24 abuts the lip 23 producing a tight fit.

Figure 5:
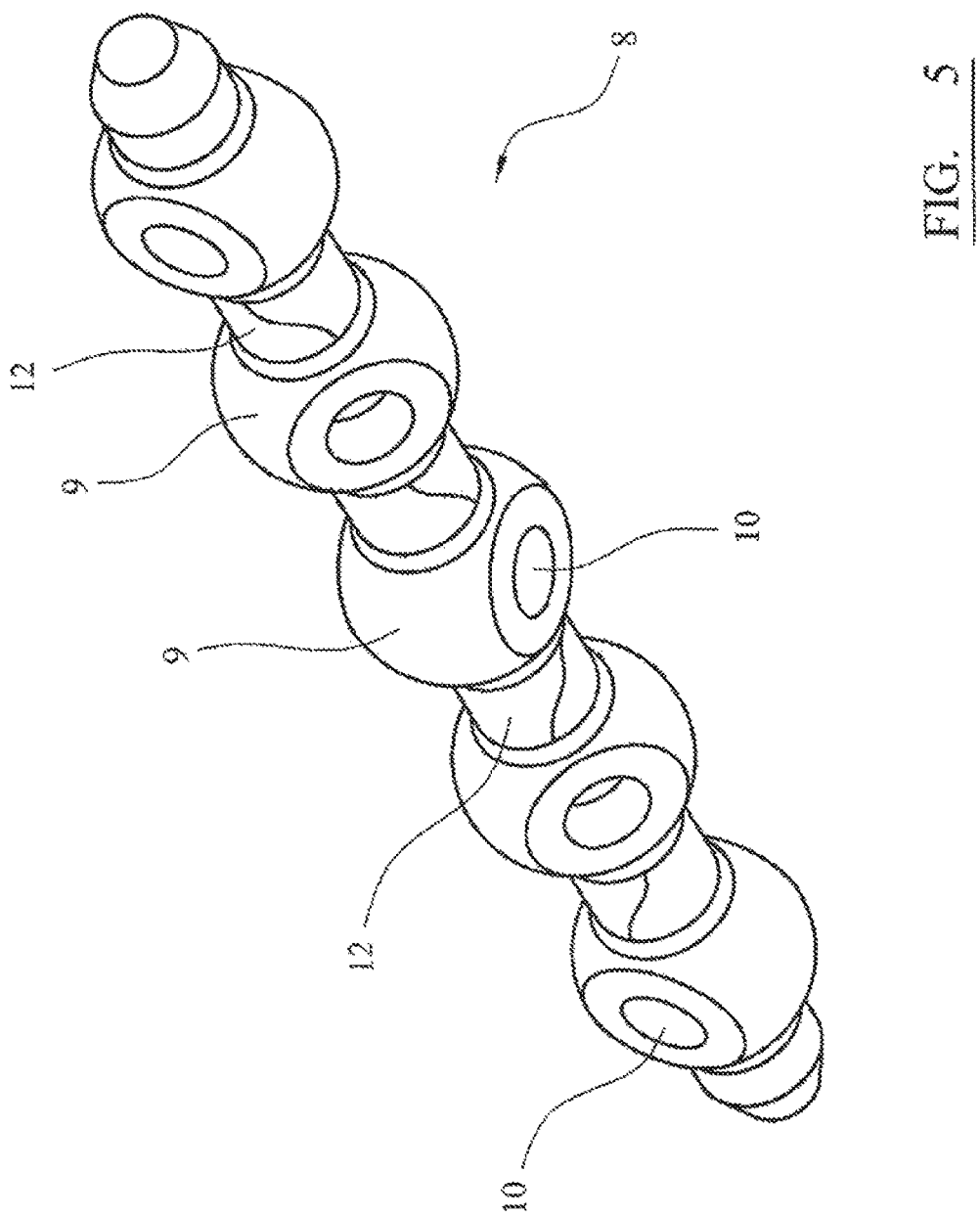
FIG. 5 shows the embodiment of FIG. 4 after twisting.

Shown in FIG. 5 is the embodiment of FIG. 4 in perspective view. The device 8 has been twisted along its length such that the apertures 10 lie in different planes. As can be seen, the arms 12 have twisted before the screw receiving members 9 deform.

In a further embodiment of the invention the screw receiving members 9 are substantially elliptical.

The device 8 according to the invention can be used with any tool which grips the screw receiving members 9. One preferred embodiment of such a tool comprises jaws having cut out sections which match the spherical components of the screw receiving members 9. The tool also has cut outs which match the interface 15 between the spherical component 9 and connecting arm 12 so that the tool can apply a bending force throughout the length of the bone fixation device 8. In an alternative embodiment the jaws have cut outs which match the flattened portions 14 of the screw receiving members 9.

In use two of the tools are used to grip the screw receiving members 9. The device 8 is then bent and/or twisted to the desired shape and then released.

Figure 6:
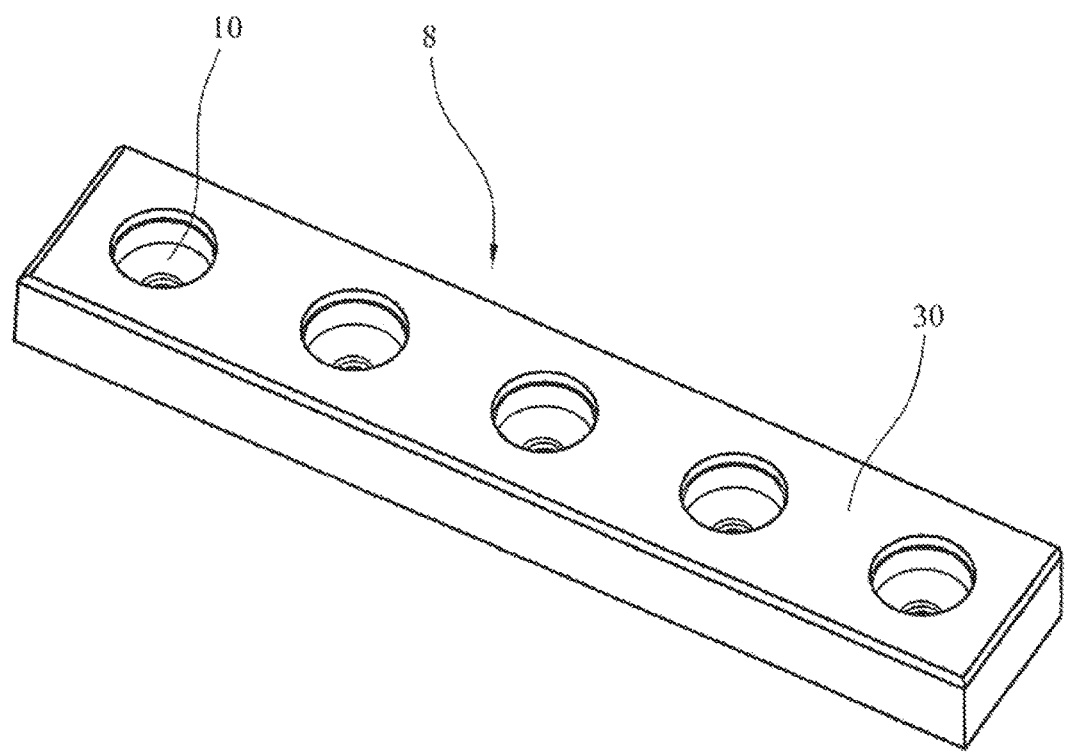
FIG. 6 shows a further embodiment of a bone fixation device according to the invention in perspective view.

Shown in FIG. 6 is a further embodiment of a bone fixation device 8 according to the invention in perspective view. In this embodiment the plastically deformable bone fixation body comprises a thick rectangular plate 30. Arranged along the plate 30 and extending through it is a plurality of screw receiving apertures 10 as shown. In use the plate 30 is deformed to approximately the same profile as the bone and then screwed to the bone by screws inserted through the apertures 10. The bone screws are tightened until the screw head abuts the wall of the aperture 10 as described in further detail with reference to FIG. 7.

Figure 7:
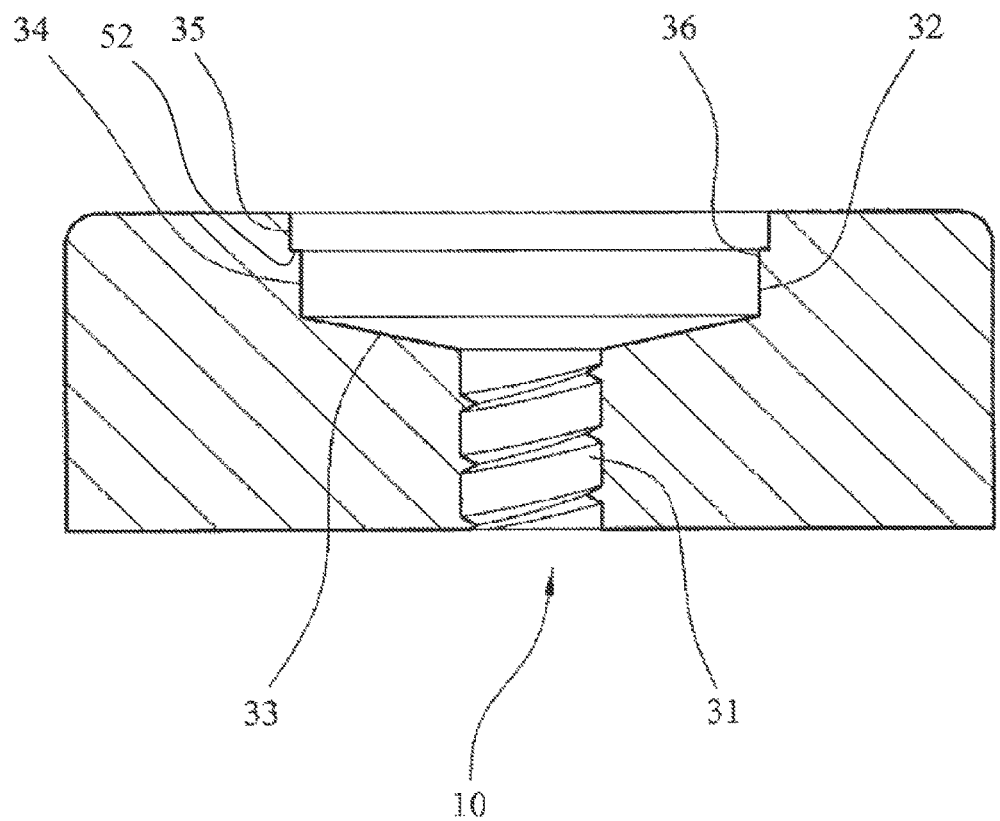
FIG. 7 shows a cross section through a screw receiving aperture of the device of FIG. 6.

Shown in FIG. 7 is a cross section through one of the screw receiving apertures 10 of the bone fixation device of FIG. 6. The aperture 10 comprises a first cylindrical threaded portion 31. Extending from the first portion 31 is a smooth cylindrical second section 32. The second section 32 comprises a conical portion 33 and then a uniform diameter portion 34. Extending from the second section 32 is a third smooth walled section 35. There is a step in cross section between the second and third sections 32, 35 defining a lip 36.

In use a screw comprising a threaded shaft and a head is inserted into the aperture 10. The threaded shaft is threaded into engagement with the first threaded portion 31 of the aperture 10. As the screw is turned the head is drawn into the aperture 10. The threaded shaft extends through the first threaded portion 31 and into the bone. As turning continues the head radially abuts the lip 36 locking the screw and bone fixation device 8 together. The head of the screw may be a domed head. Alternatively, the head of the screw may be frustoconical with the diameter of the head increasing in a direction away from the threaded shaft.

Figure 8:
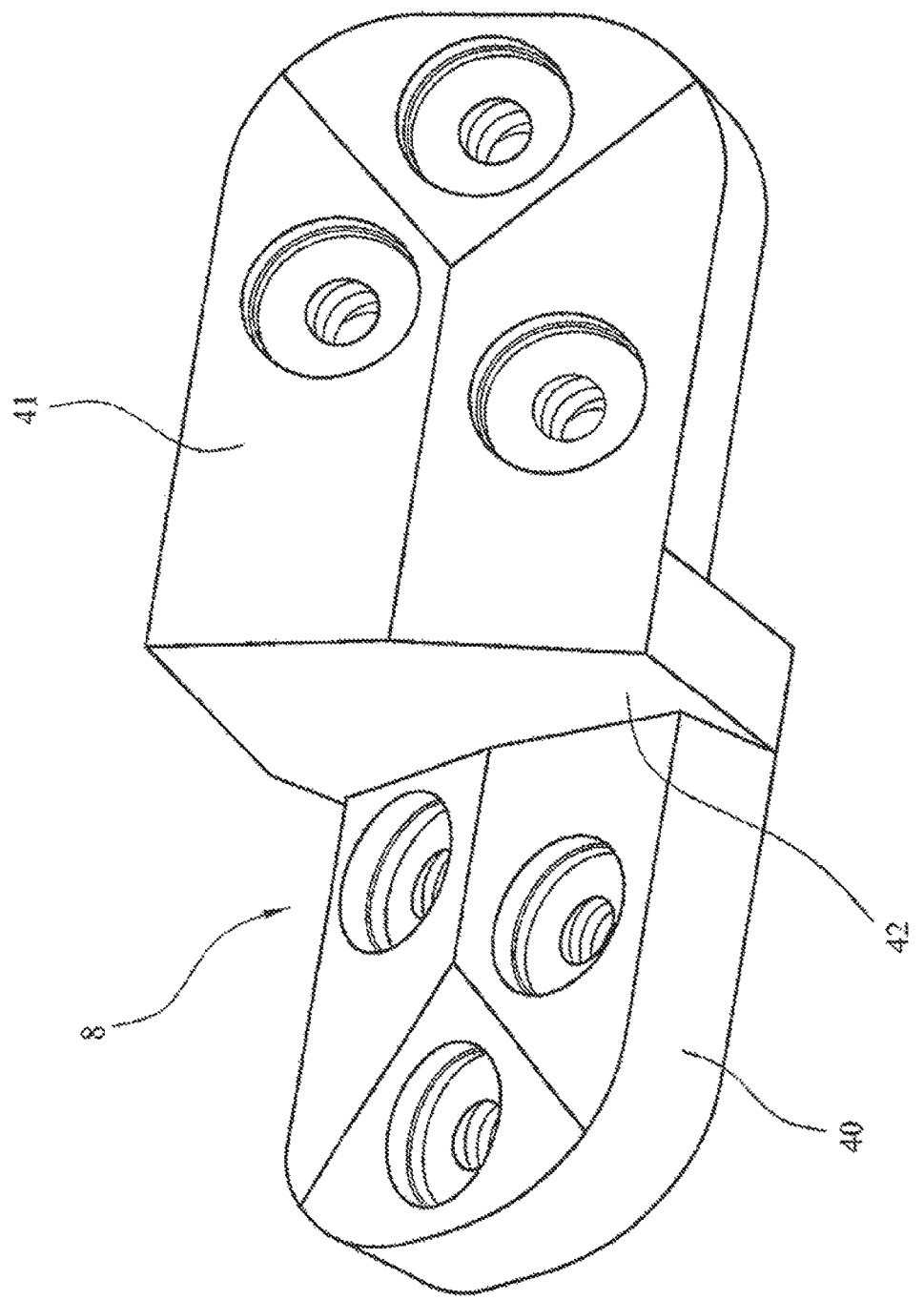
FIG. 8 shows a further embodiment of a bone fixation device according to the invention; and, FIG. 9 shows a further embodiment of a bone fixation device according to the invention.

Shown in FIG. 8 is a further embodiment of a bone fixation device according to the invention. In this embodiment the plastically deformable bone fixation body comprises two laminar members 40,41 connected together by a step 42. Each of the laminar members 40,41 comprises a plurality of screw receiving apertures 10.

Figure 9:
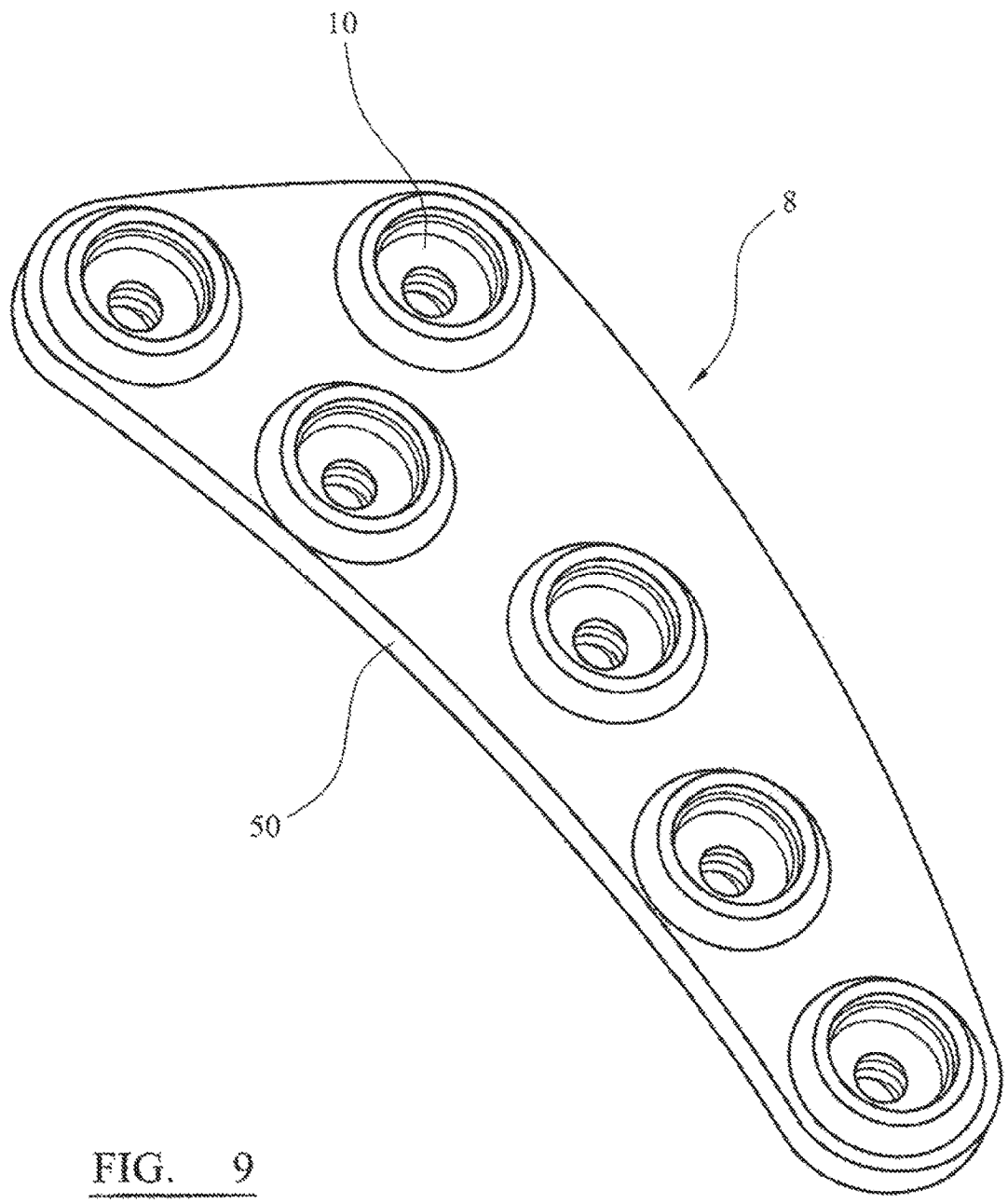

Shown in FIG. 9 is a further embodiment of a bone fixation device 8 according to the invention. In this embodiment the bone fixation body is a laminar plate 50. The plate 50 is substantially triangular in plan view having rounded corners. In this embodiment the side walls of the screw receiving apertures are upstanding from the plate 50 as shown such that the depth of the apertures 10 is greater than the thickness of the plate 50.

Embodiments in which the bone fixation body is a combination of one or more fixation bodies as described above. For example the body fixation body can be a combination of a plate portion and a further portion comprising a plurality of screw receiving members connected together by arms.

Returning to FIG. 7, as previously described the aperture comprises second and third smooth walled portions 32,35. Both of these portions 32,35 are circular in cross section in a plane normal to the length of the aperture 10. At the join between the second and third smooth walled portions 32,35 there is a discontinuity (or in other words a step change) in the size of the aperture 10 with the third smooth walled portion 35 being larger than the second smooth walled portion 32. The radius of the third smooth walled portion 35 is larger than the second 32. The second and third smooth walled portions 32,35 are connected together by a lip face 52. The plane of the lip face 52 is substantially normal to the length of the aperture 10. The angle between the side wall of the second smooth walled portion 32 and the lip face 52 is substantially 90 degrees. The edge of the lip face 52 at its point of contact with the second smooth walled portion 32 defines a lip 36.

In use the threaded portion of the screw is threaded into engagement with the threaded portion 31 of the aperture 10. As the screw head enters into the aperture 10 the screw head abuts (ie is pushed into contact with) the lip 36. This produces an abutment force. The abutment force is directed substantially radially outwards so producing a tight fit.

The invention claimed is:

1. A bone fixation device comprising
a plastically deformable bone fixation body having at least one screw receiving aperture extending therethrough, wherein the aperture is cylindrical and of constant area along its length;
the shape of the aperture being defined by a side wall, the side wall comprising a first threaded portion and a second smooth walled portion extending from the first threaded portion; and,
a bone fixation screw having a threaded shaft and a head, the shaft being adapted to engage with the first threaded portion to draw the head into the aperture, wherein the screw head is tapered with the diameter of the head increasing in a direction away from the threaded shaft;
the taper of the head of the screw being adapted such that as the screw head is drawn into the aperture the head abuts the second smooth walled portion with an abutment force which is directed substantially radially outwards, so locking the screw and aperture together.

2. A bone fixation device as claimed in claim 1, wherein the plastically deformable bone fixation body comprises a plurality of screw receiving members connected together in a line by connecting arms.

3. A bone fixation device as claimed in claim 2, wherein the screw receiving members are substantially spherical.

4. A bone fixation device as claimed in claim 3, wherein a portion of the substantially spherical member is flattened, the flattened portion being centered about a mouth of the aperture and being in a plane normal to the axis of the aperture.

5. A bone fixation device as claimed in claim 1 wherein the bone fixation body is a plate.

6. A bone fixation device as claimed in claim 1, wherein the bone fixation body comprises first and second laminar portions connected together by a step.

* * * * *